United States Patent
Xiong et al.

(10) Patent No.: US 12,156,697 B2
(45) Date of Patent: Dec. 3, 2024

(54) GLAUCOMA IMAGE RECOGNITION METHOD AND DEVICE AND DIAGNOSIS SYSTEM

(71) Applicant: SHANGHAI EAGLEVISION MEDICAL TECHNOLOGY CO., LTD., Shanghai (CN)

(72) Inventors: Jianhao Xiong, Shanghai (CN); Lijian Chen, Shanghai (CN); Yelin Huang, Shanghai (CN); Xin Zhao, Shanghai (CN); Dalei Zhang, Shanghai (CN)

(*) Notice: Subject to any disclaimer, the term of this patent is extended or adjusted under 35 U.S.C. 154(b) by 720 days.

(21) Appl. No.: 17/417,099

(22) PCT Filed: Nov. 22, 2019

(86) PCT No.: PCT/CN2019/120203
§ 371 (c)(1),
(2) Date: Jun. 21, 2021

(87) PCT Pub. No.: WO2020/125318
PCT Pub. Date: Jun. 25, 2020

(65) Prior Publication Data
US 2022/0047159 A1    Feb. 17, 2022

(30) Foreign Application Priority Data
Dec. 19, 2018   (CN) .......................... 201811554198.2

(51) Int. Cl.
*A61B 3/12* (2006.01)
*G06T 7/00* (2017.01)

(52) U.S. Cl.
CPC .............. *A61B 3/12* (2013.01); *G06T 7/0012* (2013.01); *G06T 2207/20081* (2013.01); *G06T 2207/20084* (2013.01); *G06T 2207/30041* (2013.01)

(58) Field of Classification Search
CPC .......... A61B 3/0025; A61B 3/12; A61B 3/14; A61B 3/102; A61B 3/0091; A61B 3/0016;
(Continued)

(56) References Cited

U.S. PATENT DOCUMENTS

2011/0190657 A1   8/2011   Zhou et al.
2017/0270671 A1*  9/2017   Garnavi .................. G06T 7/187
2017/0281405 A1* 10/2017   Ha .......................... A61B 3/12

FOREIGN PATENT DOCUMENTS

CN    106214120 A    12/2016
CN    106529558 A     3/2017
(Continued)

OTHER PUBLICATIONS

International Search Report Application No. PCT/CN2019/120203, dated Feb. 27, 2020, 16 pages.
(Continued)

*Primary Examiner* — Brandi N Thomas
(74) *Attorney, Agent, or Firm* — Zhong Law, LLC

(57) ABSTRACT

The present disclosure provides a glaucoma image recognition method, device and diagnosis system. The method includes acquiring a fundus image; obtaining an optic disc image and an optic cup image according to the fundus image; obtaining a disc rim image according to the optic disc image and the optic cup image; and determining whether the fundus image is classified as glaucoma according to the disc rim image.

16 Claims, 6 Drawing Sheets

(58) Field of Classification Search
CPC ..... A61B 3/0041; A61B 3/1025; A61B 3/107;
A61B 3/152; A61B 3/0008; A61B
3/1208; A61B 3/16; A61B 3/1005; A61B
5/0013; A61B 5/0066; A61B 5/6821;
A61B 3/0033; A61B 3/18; A61B 5/0015;
A61B 5/1171; A61B 2576/02; A61B
3/028; A61B 5/0075; A61B 5/4041; A61B
5/4058; A61B 5/4076; A61B 5/4082;
A61B 5/4088; A61B 5/7275; G06T
2207/30041; G06T 7/0012; G06T
2207/20084; G06T 2207/20081; G06T
7/11; G06T 2207/10024; G06T
2207/20156; G06T 7/187; G06T
2207/10101; G06T 2207/10152; G06T
2207/20221; G06T 2207/30101; G06T
7/174
See application file for complete search history.

(56) References Cited

FOREIGN PATENT DOCUMENTS

| CN | 107346545 A | 11/2017 |
| CN | 108520522 A | 9/2018 |
| CN | 108717868 A | 10/2018 |
| CN | 109549619 A | 4/2019 |
| CN | 109697716 A | 4/2019 |

OTHER PUBLICATIONS

Das et al., "Detection of glaucoma using Neuroretinal Rim information", Research Gate, IEEE, 2016, pp. 1-7.
Kavitha et al., "Neuroretinal rim Quantification in Fundus Images to Detect Glaucoma", IJCSNS, 2010, pp. 1-9.

* cited by examiner

GLAUCOMA IMAGE RECOGNITION METHOD AND DEVICE AND DIAGNOSIS SYSTEM

CROSS-REFERENCE TO RELATED APPLICATIONS

This application is the U.S. national stage of PCT/CN2019/120203 filed Nov. 22, 2019, which claims priority benefit to Chinese Patent Application No. 201811554198.2 filed Dec. 19, 2018. The contents of the above-mentioned applications are hereby incorporated by reference in their entireties.

TECHNICAL FIELD

The present disclosure relates to the field of eye detection devices, and in particular, to a glaucoma image recognition method, device and diagnosis system.

BACKGROUND

Glaucoma is an irreversible blinding fundus oculi disease. In screening or clinical diagnosis, the doctor can determine whether the examined person may suffer from glaucoma by observing a fundus image, and then make suggestions for further examination or consultation.

During clinical diagnosis, the ophthalmologist can make judgments by observing the optic cup and the optic disc in the fundus image. For example, the optic cup is too large, resulting in a too large ratio of the optic cup to the optic disc, then the examined person is likely to suffer from glaucoma, wherein the cup-disc ratio is generally a vertical diameter ratio of the optic cup to the optic disc.

However, ophthalmologist's estimation on the cup-disc ratio or the disc rim form by means of the naked eye or a shooting device is highly subjective and lacks objectivity based on data, resulting in inaccurate results and consuming a lot of time and effort.

SUMMARY

In view of this, the present disclosure provides a glaucoma image recognition method, including the following steps:
acquiring a fundus image;
obtaining, based on the fundus image, an optic disc image and an optic cup image;
obtaining a disc rim image based on the optic disc image and the optic cup image; and
determining, based on the disc rim image, whether the fundus image is classified as glaucoma.

Optionally, the obtaining, based on the fundus image, an optic disc image and an optic cup image includes:
detecting, using a first machine learning model, a valid region image including an optic disc from the fundus image, wherein an occupancy percentage of the optic disc in the valid region image is greater than the occupancy percentage of the optic disc in the fundus image;
detecting, using a second machine learning model, the optic disc image from the valid region image; and
detecting, using a third machine learning model, the optic cup image from the valid region image.

Optionally, the valid region image has the same color as the fundus image.

Optionally, the second machine learning model outputs an optic disc binary image; and the third machine learning model outputs an optic cup binary image.

Optionally, the obtaining a disc rim image based on the optic disc image and the optic cup image includes:
subtracting the optic cup binary image from the optic disc binary image to obtain a disc rim binary image.

Optionally, the obtaining a disc rim image based on the optic disc image and the optic cup image further includes:
capturing the disc rim image from the fundus image based on the disc rim binary image.

Optionally, the determining, based on the disc rim image, whether the fundus image is classified as glaucoma or not includes:
detecting, using a fourth machine learning model, the disc rim image to output a glaucoma image determination result.

The present disclosure provides a glaucoma image recognition apparatus, including:
an acquisition unit, configured to acquire a fundus image;
a region recognition unit, configured to obtain an optic disc image and an optic cup image based on the fundus image;
a disc rim determination unit, configured to obtain a disc rim image based on the optic disc image and the optic cup image; and
a glaucoma recognition unit, configured to determine, based on the disc rim image, whether the fundus image is classified as glaucoma or not.

The present disclosure further provides a glaucoma image recognition device, including: at least one processor and a memory communicatively coupled to the at least one processor; wherein the memory stores instructions executable by the at least one processor, and the instructions are executed by the at least one processor to cause the at least one processor to execute the above-mentioned glaucoma image recognition method.

The present disclosure further provides a glaucoma disease diagnosis system, including:
a fundus oculi shooting device, configured to capture a fundus image; and
the above-mentioned glaucoma image recognition device.

According to the glaucoma image recognition method provided by the embodiment of the present disclosure, an optic disc image and an optic cup image are first obtained from a fundus image, and then a disc rim image is obtained according to the two images. The disc rim image is recognized, which avoids the influence of fuzzy background and optic disc and optic cup borders and directly determines whether the fundus image is classified as glaucoma or not according to the form of the disc rim. This solution obtains a glaucoma determination result based on image data and objective algorithms, which saves human resources and can effectively assist doctors or experts in diagnosing glaucoma disease.

BRIEF DESCRIPTION OF THE DRAWINGS

In order to describe the technical solutions in the specific embodiments of the present disclosure or in the prior art more clearly, the following briefly introduces the accompanying drawings required for describing the specific embodiments or the prior art. Clearly, the accompanying drawings in the following description show only some embodiments of the present disclosure, and those of ordinary skilled in the art may still derive other drawings from these accompanying drawings without creative efforts.

DETAILED DESCRIPTION OF EMBODIMENTS

The following clearly and completely describes the technical solutions of the present disclosure with reference to the accompanying drawings. Clearly, the described embodiments are part of, not all of, the embodiments of the present disclosure. All other embodiments obtained by those of ordinary skill in the art based on the embodiments of the present disclosure without any creative effort shall fall within the protection scope of the present disclosure.

In the description of the present disclosure, it should be noted that the orientation or position relations indicated by the terms "center", "upper", "lower", "left", "right", "vertical" "horizontal", "inner", "outer", etc. are based on the orientation or position relations shown in the accompanying drawings and are intended to facilitate the description of the present disclosure and simplify the description only, rather than indicating or implying that the device or element referred to must have a particular orientation or be constructed and operated in a particular orientation, and will not to be interpreted as limiting the present disclosure. Moreover, the terms "first", "second", "third" and "fourth" are for descriptive purposes only and should not be construed as indicating or implying relative importance.

Further, the technical features involved in different embodiments of the present disclosure described below may be combined with each other as long as they do not constitute a conflict with each other.

Figure 1:
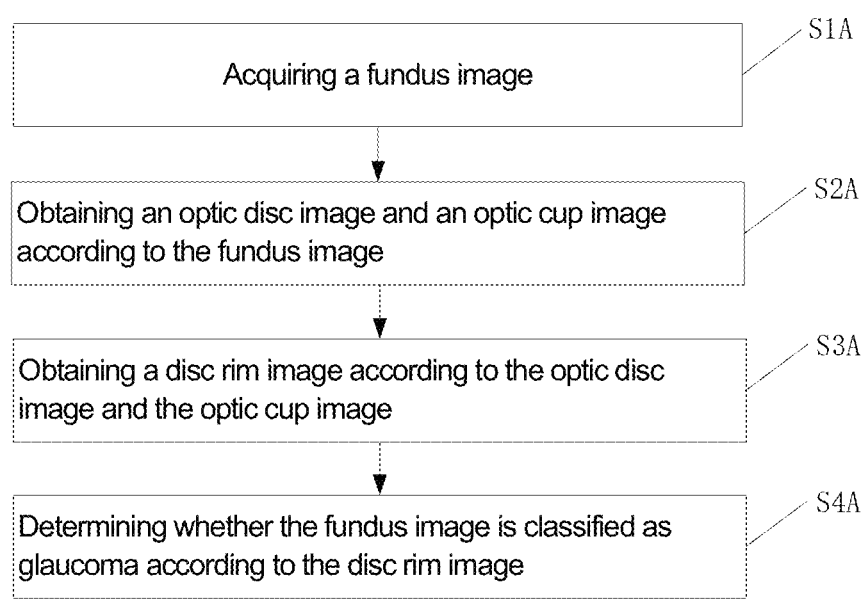
FIG. 1 is a flowchart of a glaucoma image recognition method according to an embodiment of the present disclosure.

The present disclosure provides a glaucoma image recognition method, which can be performed by an electronic device such as a computer, a server, or a portable terminal. As shown in FIG. 1, the method includes the following steps:

S1A, a fundus image is acquired. The fundus image is usually a color image, and in the embodiment of the present disclosure, it may also be a single-channel gray image or even a binary image.

S2A, an optic disc image and an optic cup image are obtained according to the fundus image. There can be a variety of specific extraction methods, for example, an optic disc region and an optic cup region are searched and extracted based on the principles of machine vision in accordance with pixel value features to form images; or the two regions are recognized and extracted using artificial intelligence algorithms and trained machine learning models to form images.

S3A, a disc rim image is obtained according to the optic disc image and the optic cup image. The optic cup region is within the optic disc region. The optic cup region is generally removed from the optic disc region to obtain an image of an annular region. The expression of a disc rim region may be an image showing only the disc rim region, for example, an annular region exists in a single-color background.

S4A, whether the fundus image is classified as glaucoma or not is determined according to the disc rim image. Based on the principles of machine vision, morphological features of some positions, for example, the left and right sides or the upper and lower ends, of the annular region in the disc rim image are extracted, and whether the fundus image is classified as glaucoma or not is determined according to these morphological features. The disc rim image can also be recognized using an artificial intelligence algorithm and a trained machine learning model to output a recognition result.

Generally, the orientation of the fundus image acquired is identical to the orientation of the human body, that is, the upper and lower parts of the image are the upper and lower parts of the human body, and the two sides of the image are the nasal side and the bitemporal of the human body (the orientations of left and right eye images are opposite). If the acquired image angle is relatively special, the image angle can be adjusted after step S1 to be identical to the orientation of the human body.

In practical applications, the output in step S4A may be a piece of information indicating the possibility of glaucoma disease, such as percentage information; or conclusive information such as negative or positive may also be outputted. This information can be used as a basis for the doctor to determine glaucoma disease.

According to the glaucoma image recognition method provided by the embodiment of the present disclosure, an optic disc image and an optic cup image are first obtained from a fundus image, and then a disc rim image is obtained according to the two images. The disc rim image is recognized, which avoids the influence of fuzzy background and optic disc and optic cup borders and directly determines whether the fundus image is classified as glaucoma or not according to the form of the disc rim. This solution obtains a glaucoma determination result based on image data and objective algorithms, which saves human resources and can effectively assist doctors or experts in diagnosing glaucoma diseases.

Figure 2:
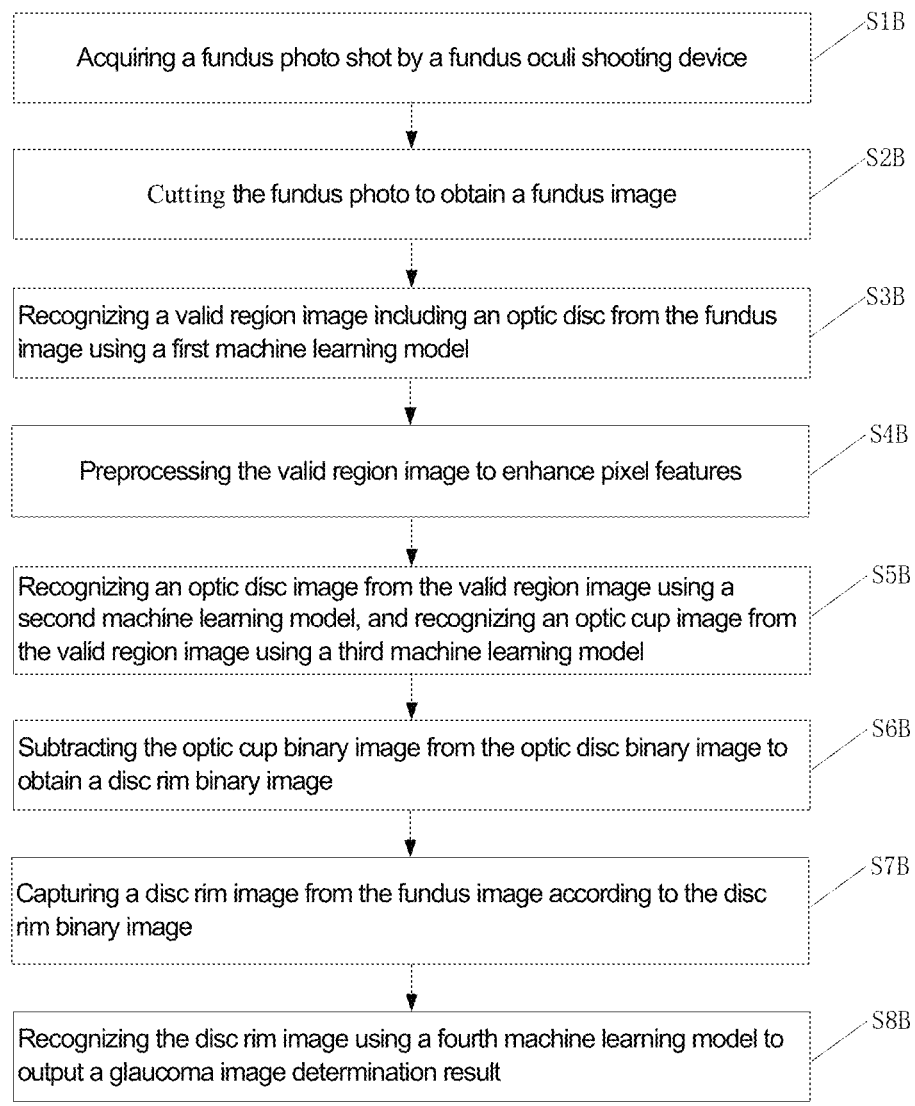
FIG. 2 is a flowchart of a detailed glaucoma image recognition method according to an embodiment of the present disclosure.

An embodiment of the present disclosure further provides a detailed glaucoma image recognition method, as shown in FIG. 2, the method including the following steps:

S1B, a fundus photo captured by a fundus oculi capture device is acquired. The fundus photo is generally an image with a black background which may include some text information.

Figure 3:
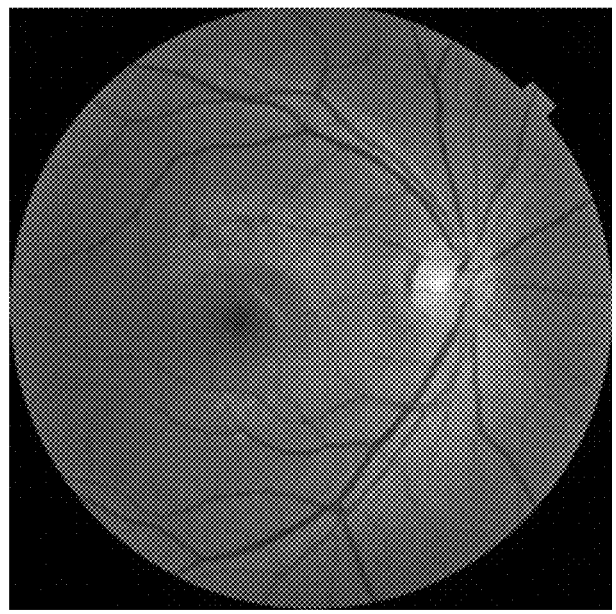
FIG. 3 is a fundus image after clipping according to an embodiment of the present disclosure.

S2B, the fundus photo is clipped to obtain a fundus image, edges of the image closely accommodating a circular fundus oculi region. As shown in FIG. 3, four edges of the clipped image intersect edges of the fundus oculi region respectively. This clipping operation is an optimization process for subsequently recognizing the image using a machine learning model, where the clipping operation may not be performed in other embodiments, or more content is clipped while at least a complete optic disc region is retained.

Figure 4:
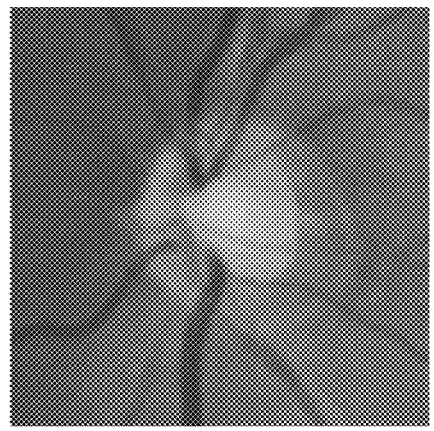
FIG. 4 is a valid region image including an optic disc according to an embodiment of the present disclosure.

S3B, a valid region image including an optic disc is detected from the fundus image using a first machine learning model. The proportion of the optic disc occupied in the valid region image is greater than the proportion of the optic disc occupied in the original fundus image. The valid region image may include the optic disc and a small portion of fundus oculi background content, and the shape of the image may be a set regular shape, such as a square image or a circular image. Most of the image background content can be removed in this step to obtain a valid region image mainly focused on the optic disc as shown in FIG. 4.

Figure 5:
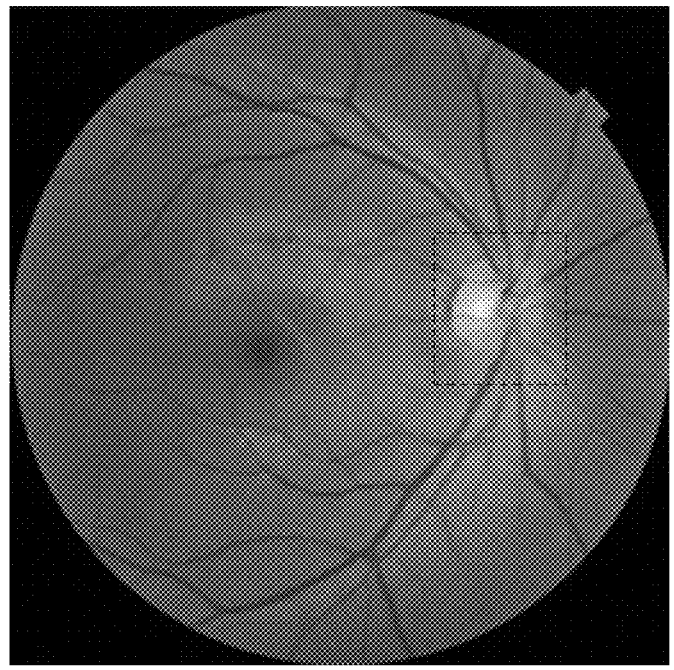
FIG. 5 is a sample image according to an embodiment of the present disclosure.

Before the machine learning model is used for detection, it should be trained with training data. With regard to the training process of the first machine learning model, the embodiment of the present disclosure provides a preferred model training scheme. In the training phase, a valid region including the optic disc is first manually labeled in the fundus image to obtain training data, for example, the dashed box shown in FIG. 5 is the label content, and the form of the label box entering the machine learning model is (x, y, height, width), where x and y are coordinates of a point at the upper left corner of the label box in the image, and height and width are respectively the height and width of the label box. A large number of fundus images and label boxes are inputted into the model together for training, where the model can predict the position of the valid region including the optic disc by means of learning to output results in the same form as the label boxes.

The embodiment of the present disclosure may employ the existing deep detection model as the first machine learning model, such as SSD, YOLO or Faster-RCNN, or construct a custom depth network model.

In this embodiment, the valid region image is consistent with the original fundus image in color, as a process of detecting and capturing an image. In other embodiments, an image with variable color channels, such as a gray image, may also be obtained.

S4B, the valid region image is preprocessed to enhance pixel features. Specifically, the valid region image may be enhanced by Contrast Limited Adaptive Histogram Equalization (CLAHE). This step can highlight the features in the image, and contours of the optic disc and the optic cup can be found more quickly during image recognition after the preprocessing, thereby improving the accuracy and efficiency of recognition.

Figure 6:
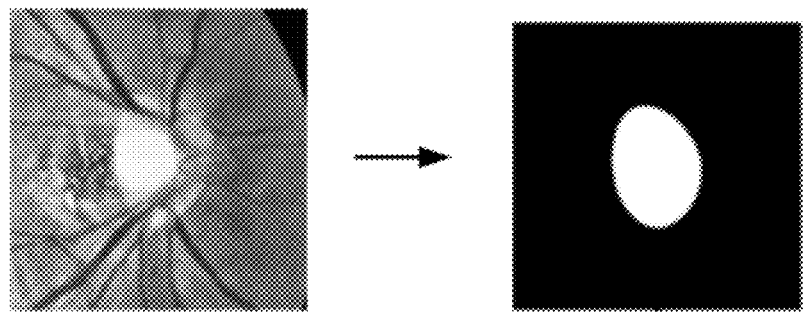
FIG. 6 is a schematic diagram of obtaining a binary image of an optic disc according to an embodiment of the present disclosure.
Figure 7:
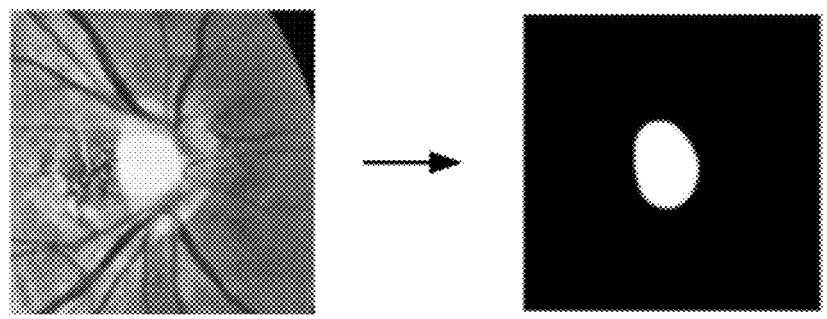
FIG. 7 is a schematic diagram of obtaining a binary image of an optic cup according to an embodiment of the present disclosure.

S5B, an optic disc image is recognized from the valid region image using a second machine learning model, and an optic cup image is recognized from the valid region image using a third machine learning model. More accurate region segmentation results are obtained in this step. The contours of the optic disc and the optic cup in the image are identical to the contours of the optic disc and the optic cup of the human body, and they are usually of irregular shapes. The optic disc image as shown in FIG. 6 and the optic cup image as shown in FIG. 7 can be obtained after recognition.

With regard to the training process of the second machine learning model and the third machine learning model, the embodiment of the present disclosure provides a preferred model training scheme. Specifically, the optic disc is precisely manually labeled during training, and then a filling mask as shown in FIG. 6 is generated based on the manually labeled contour, where the white represents the optic disc region, and the black represents the background. Finally, the clipped optic disc region and the corresponding mask are inputted into the model together for training, and the model recognizes the optic disc region by means of learning and segments it. The labeling and segmentation of the optic cup follow the same step.

The embodiment of the present disclosure may employ the existing deep detection models as the second and third machine learning models, such as U-Net, Mask R-CNN and DeepLabV3, or construct custom deep segmentation models.

In this embodiment, the second machine learning model outputs an optic disc binary image, where the grayscale value of the background is 0, and the grayscale value of the optic disc region is 255; and the third machine learning model outputs an optic cup binary image, wherein the grayscale value of the background is 0, and the grayscale value of the optic cup region is 255. This is a preferred processing method used for capturing a disc rim image later. In other embodiments, images in the same color as the original fundus image may also be outputted.

S6B, the optic cup binary image is subtracted from the optic disc binary image to obtain a disc rim binary image. For example, the binary image in FIG. 7 is subtracted from the binary image in FIG. 6 to obtain a binary image shown in FIG. 8, where the white ring represents a disc rim region. In other embodiment, two grayscale images or color images can be directly subtracted to obtain a disc rim image of the corresponding color.

Figure 8:
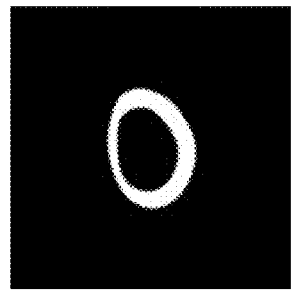
FIG. 8 is a disc rim binary image according to an embodiment of the present disclosure.
Figure 9:
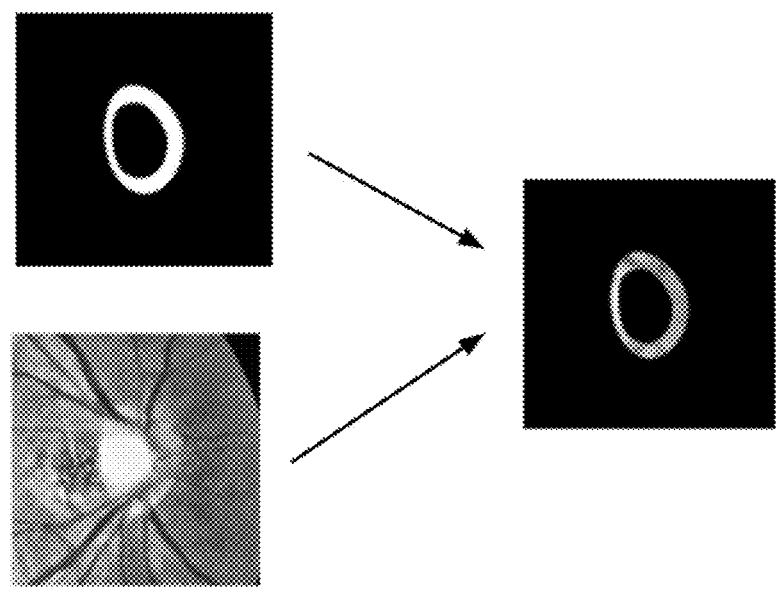
FIG. 9 is a schematic diagram of obtaining a colored disc rim image according to an embodiment of the present disclosure.

S7B, a disc rim image is captured from the fundus image according to the disc rim binary image. The disc rim binary image shown in FIG. 8 provides a capture position and range, and the disc rim image shown in FIG. 9 can be captured from the original fundus image or the valid region image in S3B. This step is to obtain the color of the original fundus image.

S8B, the disc rim image is detected using a fourth machine learning model to output a glaucoma image determination result. In this embodiment, the model recognizes the disc rim image having the same color as the original fundus image, which can take account of both the shape and color of the disc rim region and obtain the determination result. In other embodiments, the disc rim binary image can be directly recognized to obtain the determination result. Another possible embodiment may take account of only the shape of the disc rim without considering the color.

Regarding the training process of the fourth machine learning model, a disc rim region of a glaucoma image and a disc rim region of a non-glaucoma image are respectively inputted during training, so that the model learns the difference of the two and outputs a recognition result. The output result may be two types, that is, negative or positive (yes or no), or percentage (probability) information, such as a probability that the image is classified as glaucoma or the image is not a glaucoma image.

The embodiment of the present disclosure may employ the existing deep detection model as the fourth machine learning model, such as inceptionV3 or ResNet, or a custom deep recognition model.

According to the glaucoma image recognition method provided by the embodiment of the present disclosure, the captured fundus photo is first clipped to remove interference content, so that a machine learning model can more accurately segment a valid region image that is primarily based on an optic disc and that occupies a smaller region compared to the large fundus image; the valid region image is recognized by two machine learning models respectively to accurately output a binary image of an optic disc region and a binary image of an optic cup region, and the binary images are subtracted to obtain a disc rim binary image efficiently and accurately; and a disc rim image having the same color as the original fundus image is obtained based on the disc rim binary image, so that a machine learning model can consider both the shape and color features of the disc rim in the final recognition process to improve the accuracy of glaucoma image determination.

Figure 10:
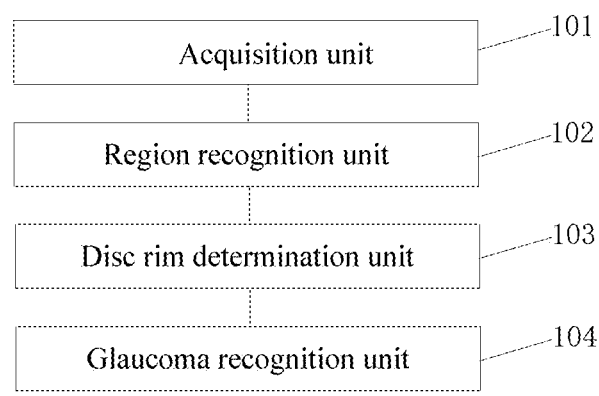
FIG. 10 is a structural diagram of a glaucoma image recognition apparatus according to an embodiment of the present disclosure.

Correspondingly, an embodiment of the present disclosure further provides a glaucoma image recognition apparatus, as shown in FIG. 10, the apparatus including:

an acquisition unit 101, configured to acquire a fundus image;

a region recognition unit 102, configured to obtain an optic disc image and an optic cup image according to the fundus image;

a disc rim determination unit 103, configured to obtain a disc rim image according to the optic disc image and the optic cup image; and a glaucoma recognition unit 104, configured to determine whether the fundus image is classified as glaucoma or not according to the disc rim image.

In a preferred embodiment, the region recognition unit 102 includes:

a first machine learning model, configured to recognize a valid region image including an optic disc from the fundus image, the proportion of the optic disc occupied in the valid region image being greater than the proportion of the optic disc occupied in the fundus image;

a second machine learning model, configured to recognize the optic disc image from the valid region image; and a third machine learning model, configured to recognize the optic cup image from the valid region image.

Further, the valid region image has the same color as the fundus image. The second machine learning model outputs an optic disc binary image; and the third machine learning model outputs an optic cup binary image.

As a preferred embodiment, the disc rim determination unit 103 includes:

an image cut unit, configured to subtract the optic cup binary image from the optic disc binary image to obtain a disc rim binary image.

Further, the disc rim determination unit 103 further includes:

an image capture unit, configured to capture the disc rim image from the fundus image according to the disc rim binary image.

In a preferred embodiment, the glaucoma recognition unit 104 includes:

a fourth machine learning model, configured to recognize the disc rim image to output a glaucoma image determination result.

An embodiment of the present disclosure further provides an electronic device, including: at least one processor and a memory communicatively coupled to the at least one processor, where the memory stores instructions executable by the at least one processor, and the instructions are executed by the at least one processor to cause the at least one processor to execute the glaucoma image recognition method in the above embodiment.

Figure 11:
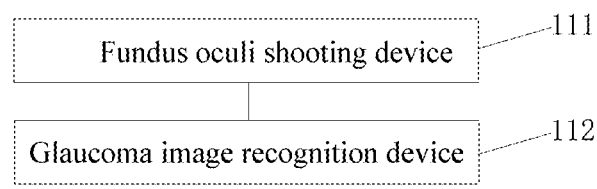
FIG. 11 is a structural diagram of a glaucoma disease diagnosis system according to an embodiment of the present disclosure.

An embodiment of the present disclosure further provides a glaucoma disease diagnosis system, as shown in FIG. 11, including:

a fundus oculi shooting device 111, configured to shoot a fundus image; and a glaucoma image recognition device 112, configured to execute the glaucoma image recognition method in the above embodiment.

A person skilled in the art should understand that the embodiments of the present disclosure may be provided as a method, a system, or a computer program product. Therefore, the present disclosure may be in the form of a full hardware embodiment, a full software embodiment, or an embodiment combining software and hardware. In addition, the present disclosure may be in the form of a computer program product implemented on one or more computer available storage media (including but not limited to a disk memory, a CD-ROM, an optical memory, and the like) including computer available program codes.

The present disclosure is described with reference to flow diagrams and/or block diagrams of the method, equipment (system), and the computer program product in the embodiments of the present disclosure. It should be understood that computer program instructions can implement each process and/or block in the flowcharts and/or block diagrams and a combination of processes and/or blocks in the flowcharts and/or block diagrams. These computer program instructions may be provided to a general-purpose computer, a dedicated computer, an embedded processor, or a processor of other programmable data processing equipment to generate a machine, so that a device configured to implement functions specified in one or more processes in the flowcharts and/or one or more blocks in the block diagrams is generated by using instructions executed by the general-purpose computer or the processor of other programmable data processing equipment.

These computer program instructions may also be stored in a computer readable memory that can guide a computer or other programmable data processing equipment to work in a specific manner, so that the instructions stored in the computer readable memory generate a product including an instruction device, where the instruction device implements functions specified in one or more processes in the flowcharts and/or one or more blocks in the block diagrams.

These computer program instructions may also be loaded into a computer or other programmable data processing equipment, so that a series of operation steps are performed on the computer or other programmable data processing device to generate processing implemented by a computer, and instructions executed on the computer or other programmable data processing equipment provide steps for implementing functions specified in one or more processes in the flowcharts and/or one or more blocks in the block diagrams.

It is apparent that the above embodiments are merely illustrative of the examples, and are not intended to limit the embodiments. Other variations or modifications of different forms may be made by those of ordinary skill in the art in light of the above description. There is no need and no way to exhaust all of the embodiments. Obvious variations or modifications resulting therefrom are still within the scope of the present disclosure.

What is claimed is:

1. A method for recognizing glaucoma, the method comprising:
    acquiring a fundus image;
    obtaining, based on the fundus image, an optic disc image and an optic cup image;
    obtaining a disc rim image based on the optic disc image and the optic cup image; and
    utilizing a machine learning model to determine, based on the disc rim image, whether the fundus image is classified as glaucoma or not;

wherein the machine learning model outputs a classification result on whether the fundus image is a glaucoma image based on the shape and color features of the disc rim image, and the machine learning model is trained based on a disc rim region labeled as glaucoma and a disc rim region labeled as non-glaucoma.

2. The method according to claim 1, wherein the obtaining, based on the fundus image, an optic disc image and an optic cup image further comprises:
detecting, using a first machine learning model, a valid region image including an optic disc from the fundus image, wherein a proportion of the optic disc occupied in the valid region image is greater than the proportion of the optic disc occupied in the fundus image;
detecting, using a second machine learning model, the optic disc image from the valid region image; and
detecting, using a third machine learning model, the optic cup image from the valid region image.

3. The method according to claim 2, wherein the valid region image has a same color as the fundus image.

4. The method according to claim 2, wherein the second machine learning model outputs an optic disc binary image, and the third machine learning model outputs an optic cup binary image.

5. The method according to claim 4, wherein the obtaining a disc rim image based on the optic disc image and the optic cup image comprises:
subtracting the optic cup binary image from the optic disc binary image to obtain a disc rim binary image.

6. The method according to claim 5, wherein the obtaining a disc rim image based on the optic disc image and the optic cup image further comprises:
capturing the disc rim image from the fundus image based on the disc rim binary image.

7. The method according to claim 1, wherein the determining, based on the disc rim image, whether the fundus image is classified as glaucoma or not further comprises:
detecting, using a fourth machine learning model, the disc rim image to output a glaucoma image determination result.

8. A non-transitory computer storage medium, storing instructions thereon that, when executed on a computer, cause the computer to perform operations comprising:
acquiring a fundus image;
obtaining, based on the fundus image, an optic disc image and an optic cup image;
obtaining a disc rim image based on the optic disc image and the optic cup image; and
utilizing a machine learning model to determine, based on the disc rim image, whether the fundus image is classified as glaucoma or not;
wherein the machine learning model outputs a classification result on whether the fundus image is a glaucoma image based on the shape and color features of the disc rim image, and the machine learning model is trained based on a disc rim region labeled as glaucoma and a disc rim region labeled as non-glaucoma.

9. A glaucoma image recognition device, comprising: at least one processor and a memory communicatively coupled to the at least one processor, wherein the memory stores instructions executable by the at least one processor, and the instructions are executed by the at least one processor to:
acquire a fundus image;
obtain, based on the fundus image, an optic disc image and an optic cup image;
obtain a disc rim image based on the optic disc image and the optic cup image; and
utilizing a machine learning model to determine, based on the disc rim image, whether the fundus image is classified as glaucoma or not;
wherein the machine learning model outputs a classification result on whether the fundus image is a glaucoma image based on the shape and color features of the disc rim image, and the machine learning model is trained based on a disc rim region labeled as glaucoma and a disc rim region labeled as non-glaucoma.

10. A glaucoma disease diagnosis system, comprising:
a fundus oculi photographing device, configured to capture a fundus image; and
the glaucoma image recognition device according to claim 9.

11. The glaucoma image recognition device according to claim 9, wherein to obtain, based on the fundus image, an optic disc image and an optic cup image, the at least one processor is further to:
detect, using a first machine learning model, a valid region image including an optic disc from the fundus image, wherein a proportion of the optic disc occupied in the valid region image is greater than the proportion of the optic disc occupied in the fundus image;
detect, using a second machine learning model, the optic disc image from the valid region image; and
detect, using a third machine learning model, the optic cup image from the valid region image.

12. The glaucoma image recognition device according to claim 11, wherein the valid region image has a same color as the fundus image.

13. The glaucoma image recognition device according to claim 11, wherein the second machine learning model outputs an optic disc binary image, and the third machine learning model outputs an optic cup binary image.

14. The glaucoma image recognition device according to claim 13, wherein to obtain a disc rim image based on the optic disc image and the optic cup image, the at least one processor is further to subtract the optic cup binary image from the optic disc binary image to obtain a disc rim binary image.

15. The glaucoma image recognition device according to claim 14, wherein to obtain a disc rim image based on the optic disc image and the optic cup image, the at least one processor is further to capture the disc rim image from the fundus image based on the disc rim binary image.

16. The glaucoma image recognition device according to claim 9, wherein to determine, based on the disc rim image, whether the fundus image is classified as glaucoma or not, the at least one processor is further to detect, using a fourth machine learning model, the disc rim image to output a glaucoma image determination result.

* * * * *